(12) United States Patent
Tokunaga et al.

(10) Patent No.: US 7,504,020 B2
(45) Date of Patent: Mar. 17, 2009

(54) DETERMINATION METHOD FOR AUTOMATICALLY IDENTIFYING ANALYTE LIQUID AND STANDARD SOLUTION FOR BIOSENSOR

(75) Inventors: Hiroyuki Tokunaga, Ehime (JP); Motonori Uchiyama, Ehime (JP); Eriko Yamanishi, Ehime (JP); Shoji Miyazaki, Matsuyama (JP)

(73) Assignee: Panasonic Corporation, Osaka (JP)

( * ) Notice: Subject to any disclaimer, the term of this patent is extended or adjusted under 35 U.S.C. 154(b) by 444 days.

(21) Appl. No.: 10/523,076

(22) PCT Filed: Oct. 31, 2003

(86) PCT No.: PCT/JP03/13991

§ 371 (c)(1),
(2), (4) Date: Jan. 25, 2005

(87) PCT Pub. No.: WO2004/040286

PCT Pub. Date: May 13, 2004

(65) Prior Publication Data

US 2005/0247562 A1    Nov. 10, 2005

(30) Foreign Application Priority Data

Oct. 31, 2002    (JP) .............................. 2002-318173

(51) Int. Cl.
*G01N 27/327*    (2006.01)
(52) U.S. Cl. .................... 205/792; 204/403.02; 204/406
(58) Field of Classification Search ............ 204/403.01, 204/403.02, 406; 205/792
See application file for complete search history.

(56) References Cited

U.S. PATENT DOCUMENTS

| | | | | |
|---|---|---|---|---|
| 5,120,420 | A | * | 6/1992 | Nankai et al. .......... 204/403.11 |
| 5,723,284 | A | * | 3/1998 | Ye ................................ 435/4 |
| 7,232,510 | B2 | * | 6/2007 | Miyazaki et al. ....... 204/403.01 |

FOREIGN PATENT DOCUMENTS

| | | |
|---|---|---|
| EP | 1 156 324 | 11/2001 |
| EP | 1 256 798 | 11/2002 |

(Continued)

*Primary Examiner*—Kaj K Olsen
(74) *Attorney, Agent, or Firm*—Wenderoth, Lind & Ponack, L.L.P.

(57) ABSTRACT

According to the standard solution and the determination method of the present invention, in a case where a voltage is applied by a drive voltage of a measurement apparatus to an electrode portion of a biosensor comprising an electrode portion including a counter electrode and a measuring electrode formed on an insulating substrate, and a reagent layer which reacts with a sample solution supplied to the electrode portion, and a current value which flows at the application is measured, thereby determining a substrate contained in the sample solution, a reducing substance is contained in the standard solution used for controlling a precision of measurement of the measurement apparatus. Therefore, when the standard solution is measured, a large change occurs in a current waveform between time t0 and t1 shown in FIG. 6 due to the reducing substance, thereby discriminating whether the analyte liquid being measured is the standard solution or the sample solution and easily identifying the kind of analyte liquid.

8 Claims, 5 Drawing Sheets

FOREIGN PATENT DOCUMENTS

| | | |
|---|---|---|
| JP | 02245650 | 10/1990 |
| JP | 03287064 | 12/1991 |
| JP | 11304748 | 11/1999 |
| WO | 93/21928 | 11/1993 |
| WO | 95/13536 | 5/1995 |
| WO | 01/40787 | 6/2001 |
| WO | 02/44705 | 6/2002 |

\* cited by examiner

DETERMINATION METHOD FOR AUTOMATICALLY IDENTIFYING ANALYTE LIQUID AND STANDARD SOLUTION FOR BIOSENSOR

This application is U.S. national phase application of PCT International Application PCT/JP 03/13991, filed on Oct. 31, 2003.

TECHNICAL FIELD

The present invention relates to a determination method for, in electrochemically determining the content of substrate in the analyte liquid supplied to a biosensor by a measurement apparatus for the biosensor, automatically discriminating whether the analyte liquid is sample solution as a target to be measured or standard solution for controlling the precision of measurement of the measurement apparatus. More particularly, the present invention relates to a determination method for automatically identifying the kind of analyte liquid, which can reduce errors in identifying the kind of analyte liquid due to errors in measuring the content of substrate in the analyte liquid, and the standard solution for the biosensor.

BACKGROUND ART

A biosensor is a sensor which applies a biological material as a molecule identification element by utilizing a molecule identification function of the biological material such as a microorganism, an enzyme, an antibody, a DNA, and an RNA to determine the content of substrate in an analyte. That is, the biosensor determines the content of the substrate contained in the analyte with utilizing a reaction which occurs when the biological material identifies the target substrate, such as oxygen consumption caused by a respiration of a microorganism, an enzyme reaction, light emission and the like.

Among various biosensors described above, practical use of an enzyme sensor which is a biosensor for such as glucose, lactic acid, cholesterol, and amino acid is advancing, and the enzyme biosensor is utilized for medical measurement and food industry. The enzyme sensor reduces electron transporters by electrons which are generated by reactions between the substrate (for example, glucose) contained in the analyte (for example, sample solution such as blood) and the enzyme or the like, and the measurement apparatus for the enzyme sensor electrochemically measures an amount of reduction of the electron transporters, thereby quantitatively analizing the content of the substrate in the analyte.

As described above, the determination of the substrate contained in body fluid of a human body is very important for a diagnosis or a therapy for a specific physiological abnormality. Specifically, it is necessary for a diabetic to frequently comprehend the concentration of glucose in the blood.

Conventionally, various types of the biosensors are proposed. Hereinafter, a prior art biosensor will be described with reference to FIG. 1. FIG. 1(a) is an exploded perspective view illustrating a construction of a biosensor, and FIG. 1(b) is a plan view of the biosensor shown in FIG. 1(a).

In FIG. 1(a), a biosensor 15 comprises an insulating substrate 1 made of polyethylene terephthalate and the like (hereinafter, merely referred to as "a substrate"), a spacer 6 having a notch 7, an insulating substrate 8 provided with an air hole 9, and a reagent layer 5, which are integrally positioned with the spacer 6 and the reagent layer 5 being sandwiched between the insulating substrate 8 and the substrate 1.

A conductive layer 10 made of an electrically conductive material such as precious metal like gold or palladium or carbon is formed on the surface of the substrate 1 by using a screen printing method or a sputtering vapor deposition method, and the conductive layer 10 on the substrate 1 is divided by plural slits to produce a counter electrode 3, a measuring electrode 2 and a detection electrode 4. Then, substantially arc-shaped slits 13 and 14 are formed on the counter electrode 3. While FIG. 1 shows that the conductive layer 10 is provided on the whole surface of the substrate 1, the conductive layer 10 may be formed on a part of the substrate 1, and the respective electrodes 2, 3, and 4 may be formed on parts of the substrate 1.

The spacer 6 is positioned so as to cover the counter electrode 3, the measuring electrode 2 and the detection electrode 4 on the substrate 1. Then, an analyte supply path 7a is produced by the rectangular notch 7 provided at the center of the front edge of the spacer 6. When a sample solution such as blood which is an analyte is spotted onto an analyte spot portion 15a which is positioned at an end of the analyte supply path 7a, the sample solution is substantially horizontally sucked toward the air hole 9 due to a capillary phenomenon.

The reagent layer 5 is produced by applying a reagent containing an enzyme, an electron acceptor, a hydrophilic high polymer and the like onto the counter electrode 3, the measuring electrode 2, and the detection electrode 4 on the substrate 1, which are exposed from the notch 7 of the spacer 6, and a spread of the applied reagent on the substrate 1 is controlled by the arc-shaped slits 13 and 14 which are formed on the counter electrode 3.

Here, as an enzyme to be contained in the reagent, glucose oxidase, lactate oxidase, cholesterol oxidase, cholesterol esterase, uricase, ascorbic acid oxidase, bilirubin oxidase, glucose dehydrogenase, lactate dehydrogenase and the like can be used. Further, while potassium ferricyanide is preferably used as the electron accepter, p-benzoquinone and a derivative thereof, phenazine methyl sulfate, methylene blue, ferrocene and a derivative thereof, and the like, may be used other than potassium ferricyanide. The specific examples of the enzyme and the electron accepter contained in the reagent layer 5 of the biosensor 15, which are cited here, are particularly suitable for determining a content of glucose, lactic acid, and cholesterol which are substrates contained in blood of a human body as an analyte. When, for example, a glucose in blood of a human body is determined using this biosensor 15, glucose dehydrogenase and potassium ferricyanide are used as an oxidation-reduction enzyme and an electron accepter which are to be contained in the reagent layer 5, respectively.

Hereinafter, a case where the content of a substrate in an analyte is determined using the biosensor 15 having the above-described construction will be described. While a case where glucose contained in blood of a human body is determined using the biosensor 15 is described, lactic acid, cholesterol, or other substrates can also be determined with appropriately selecting an enzyme contained in the reagent layer 5 of the biosensor 15.

Initially, when a blood taken from a human body is spotted onto the analyte spot portion 15a of the analyte supply path 7a of the biosensor 15, the oxidation-reduction enzyme, i.e., glucose dehydrogenase and the electron accepter, i.e., potassium ferricyanide which are contained in the reagent layer 5 are dissolved into the blood which is sucked in the analyte supply path 7a, and thereby an enzyme reaction proceeds between the glucose which is a substrate in the blood and the oxidation-reduction enzyme, and further, the enzyme reaction makes the potassium ferricyanide serving as an electron accepter reduced thereby to generate ferrocyanide (potassium ferrocyanide). Then, a series of these reactions (the enzyme reaction of the oxidation-reduction enzyme, and the reduction of the electron accepter) mainly proceed in the analyte supply path 7a.

Then, the above-described reduced potassium ferrocyanide which was serving as an electron accepter is electrochemically oxidized and a current value which is obtained this time with associated with the above-described electrochemical change is read by the counter electrode 3, the measuring electrode 2, and the detection electrode 4 on the conductive layer 10 in a measurement apparatus for a biosensor, which will be described later, and thereby the concentration of glucose in the blood is measured on the basis of the current value.

Then, the determination of the substrate in the analyte liquid is performed by inserting the biosensor 15 into the measurement apparatus 16 for the biosensor as shown in FIG. 2.

Hereinafter, an operation for determining glucose in blood of a human body with a biosensor system comprising the biosensor 15 and the measurement apparatus 16 for biosensor will be described with reference to FIG. 2. FIG. 2 is a diagram illustrating a construction of a prior art biosensor system.

Initially, the construction of the biosensor will be described. As shown in FIG. 2, the biosensor system comprises the above-described biosensor 15 and the measurement apparatus 16 for the biosensor to which the biosensor 15 is detachably mounted, and it determines an amount of substrate contained in an analyte spotted onto the analyte spot portion 15a of the biosensor 15 with the measurement apparatus 16. Then, the measurement apparatus 16 for biosensor comprises an insertion portion 17 to which the biosensor 15 is detachably mounted, a driving power supply (not shown) for applying a voltage to the electrodes of the biosensor, and a display unit 18 which displays the result of determining the substrate in the analyte, which is obtained by applying the voltage by the driving power supply. Then, the measurement apparatus 16 for the biosensor and the respective electrodes of the biosensor 15 may be connected through lead wires.

In a case where the content of substrate such as glucose in blood is determined using a biosensor of such construction, a user initially inserts the biosensor 15 into the measurement apparatus 16. Then, the user spots blood onto the analyte spot portion 15a in a state where a constant voltage is applied between the counter electrode 3 and the measuring electrode 2 on the substrate 1 of the biosensor 15 in the measurement apparatus 16. The spotted blood is sucked into the inside of the biosensor 15 toward the air hole 9, and thereby the reagent layer 5 starts to be dissolved.

At this time, the measurement apparatus 16 detects an electrical change which occurs between the electrodes 2 and 3 in the biosensor 15, to start the determination operation.

In the measurement apparatus 16 for the biosensor, a constant voltage is applied between the electrodes 2 and 3 in the biosensor 15 which is inserted into the measurement apparatus 16, and it is detected that a sample solution which is blood is spotted onto the analyte spot portion 15a of the analyte supply path 7a, which is an enzyme reaction layer of the biosensor 15. Then, application of a voltage between the electrodes 2 and 3 is temporarily halted, and a constant voltage is again applied after a given time period, and then a current which flows between the electrodes 2 and 3 is measured, and thereby glucose in the blood is determined and the blood sugar level is calculated (for example, refer to claim 2 of the Japanese Published Patent Application No. Hei. 3-287064).

As a performance which is recently requested for such a biosensor system, further shortening of the measurement time is raised.

When determination of substrate in blood is performed by the above-described biosensor at high speed, the viscosity of the blood as an analyte affects substantial influences upon the precision of measurement. As a determination method which can solve these problems and enables performing a high precision measurement with that biosensor, a method is disclosed in which the measurement apparatus 16 applies a first potential between the counter electrode 3 and the measuring electrode 2 in the biosensor for a first time period, and then application of the potential is halted for a waiting period, and a second potential which is lower than the first potential is applied between the counter electrode 3 and the measuring electrode 2 for a second time period after the passage of the waiting period, and thereby an output current is measured (for example, refer to claim 21 of the International Application Publication No. WO02/44705A1).

Recently, a commodity product having various different functions is developed as a compact and simple blood sugar level measurement system for determining the blood sugar level. For example, an importance is placed especially upon a field of data management such as management and processing of the measurement data in the blood sugar level measurement system. Generally, for the biosensor system comprising the above-described biosensor and measurement apparatus for the biosensor, the administration of the precision of measurement is periodically performed using its dedicated standard solution so as to maintain and control the precision of measurement.

Here, as the conventional standard solution for the biosensor, one containing water, a predetermined amount of glucose, xanthan, and phosphate as a reaction rate modifier is disclosed (for example, refer to claim 1 of the International Application Publication No. WO93/21928-A). Further, as another example, serum-free control reagent containing a mixture of a predetermined amount of glucose used for measuring the glucose, water, a thickener, a buffer, a preservative, a surface-active agent, a coloring or color-forming compound, and the like are disclosed (for example, refer to claims 1 to 8 of the International Application Publication No. WO95/13536-A).

Then, in the prior art biosensor system which controls the precision of measurement of the measurement apparatus using the standard solution, in order to prevent the measurement data of the standard solution from being confused in being processed with the measurement data of the body fluid and the like used as a normal sample solution, the measurement apparatus is previously switched to a measurement mode for the standard solution with a predetermined manual operation when the standard solution is introduced into the biosensor system, and thereby the measurement data of the standard solution and the measurement data of the sample solution are distinguished from each other.

On the other hand, in recent years, a means for automatically identifying the kind of analyte liquid is provided. Disclosed as that method is one in which a ratio between a current value which is measured for each sample solution that is an analyte and a value obtained by time-differentiating the current value is set as a discrimination parameter for discriminating between the respective analyte liquids, and a discrimination function employing the discrimination parameter as an independent variable is defined for discriminating among plural kinds of target analyte liquids, and a numeric value which is obtained by substituting the value of the discrimination parameter into the discrimination function is taken as a discrimination index, and thereby the kinds of samples are automatically discriminated on the basis of the discrimination index. (For example, refer to claim 1 of International Application Publication No. WO01/40787A1).

However, the above-described method for automatically identifying the kind of analyte liquid cannot accomplish the identification of the kind of analyte liquid with high precision due to the following various factors, and the method is not currently put into practical use.

Hereinafter, the factors will be specifically described with reference to FIG. 3. FIG. 3 is a diagram illustrating waveforms of oxidation current values which are measured when a voltage is applied to the biosensor onto which a conventional standard solution or bloods under various conditions are spotted in the biosensor system. FIG. 3(a) shows current waveforms of a conventional standard solution a and three kinds of bloods b to d having different hematocrit values from each other, FIG. 3(b) shows current waveforms of the conventional sample solution a and three kinds of bloods e to f containing different interfering substances from each other, and FIG. 3(c) shows current waveforms of the conventional standard solution a and three kinds of bloods h to j having different environmental temperatures from each other. Then, the measurement shown in FIG. 3 is performed on the basis of a measurement profile shown in FIG. 4. More specifically, as indicated in the above-described International Application Publication No. WO02/44705A1, the measurement apparatus 16 applies a first potential between the counter electrode 3 and the measuring electrode 2 of the biosensor onto which the respective analytes are spotted for a first potential time period (from time t0 to t1), and thereafter stops the application for a waiting period (from time t1 to t2), and applies a second potential which is lower than the first potential for a second potential time period (from time t2 to t3) after the waiting period has passed. Here, the measurement is performed under conditions where the first potential is 0.5V and the second potential is 0.2V, and the first potential time period is 6 seconds, the waiting period is 6 seconds, and the second potential time period is 3 seconds. However, it is required to appropriately set the applied potential and the application time period in accordance with the electrode materials used for the biosensor 15 as well as conditions of the reagent layer 5.

Initially, as a first factor, personal differences in the constituent components of bloods which are used as sample solutions are raised.

Since the hematocrit values which exert influences onto the viscosities of the bloods vary among users, the current waveforms of bloods having different hematocrit values from each other show various shapes as shown by the waveforms b to d in FIG. 3(a). Then, in FIG. 3(a), "a" denotes a current waveform of a conventional sample solution, "b" denotes a current waveform of a blood having hematocrit value of 20%, "c" denotes a current waveform of a blood having hematocrit value of 45%, and "d" denotes a current waveform of a blood having hematocrit value of 60%.

Further, since various substances called interfering substances which exert influences onto the measurement values, such as ascorbic acid, uric acid, and bilirubin, vary among the users, the current waveforms of bloods containing the above-described interfering substances show various shapes as shown by the waveforms e to g in FIG. 3(b). Then, in FIG. 3(b), "e" denotes a current waveform of a blood containing ascorbic acid (10 mg/dl), "f" denotes a current waveform of a blood containing uric acid (10 mg/dl), and "g" denotes a current waveform of a blood containing bilirubin (10 mg/dl).

As a result, as is apparent from FIGS. 3(a) and 3(b), there is little difference between the current waveform a of the conventional standard solution and the current waveforms b to g of the bloods which vary among individuals as described above, which makes it difficult to discriminate between the conventional standard solution and the respective sample solutions with high precision.

Secondly, as a second factor, environmental conditions under which the users use the blood sugar measurement system are different from each other.

The blood sugar measurement system is used under environmental conditions which would vary among the users. In a case where the environmental conditions where it is used, for example, environmental temperatures, are wide-ranging (for example, 10° C. to 40° C.), the solubility of the substrate contained in the analyte liquid and the reagent layer as well as the reaction rate thereof vary depending on the environmental temperatures, and therefore the current waveforms of bloods having different environmental conditions from each other show various shapes as shown by the waveforms h to j in FIG. 3(c). In FIG. 3(c), "h" denotes a current waveform of a blood having environmental temperature of 40° C., "i" denotes a current waveform of a blood having environmental temperature of 25° C., and "j" denotes a current waveform of a blood having environmental temperature of 10° C. As with the above description, also in this case, as is apparent from FIG. 3(c), there is little difference between the current waveform a of the conventional standard solution and the current waveforms h to j of the bloods having different environmental conditions from each other, which makes it difficult to discriminate between the conventional standard solution and the respective sample solutions with high precision. Then, the environmental temperature of the conventional standard solution a shown in FIG. 3(c) is 25° C.

As described above, the current waveform of the conventional standard solution is very similar to the current waveforms of the bloods as sample solution under various conditions. Therefore, in a case where the measurement apparatus 16 automatically discriminates whether the kind of analyte liquid being measured is a standard solution or a sample solution, on the basis of the current waveforms obtained from the measurement, an error in identifying the kind of analyte liquid is likely to occur. Therefore, the prior art measurement apparatus 16 must be constructed so that it may be switched to a measurement mode with manual operation, as described above.

The present invention is made in view of the above-described problems, and has its object to provide standard solution for a biosensor, which has high precision and can eliminate errors in identifying the kind of analyte liquid, and a determination method for automatically identifying the kind of analyte liquid using the standard solution.

DISCLOSURE OF THE INVENTION

In order to solve the above-described problems, a standard solution according to the present invention is a standard solution which is used for controlling a precision of measurement of a measurement apparatus which determines a substrate contained in a sample solution with applying a voltage by a driving power supply to an electrode portion of a biosensor, the biosensor including the electrode portion having a measuring electrode and a counter electrode, as well as a reagent layer reacting with the sample solution supplied to the electrode portion, and thereby electrochemically measuring a reaction between the sample solution and the reagent layer, wherein said standard solution includes reducing substance.

Therefore, it is possible to provide standard solution enabling the measurement apparatus to easily accomplish identification of the kind of analyte liquid without no identification error occurring, which was conventionally difficult.

Further, according to the standard solution of the present invention, when a first potential is applied to the electrode portion of the biosensor to which the standard solution is supplied, by the driving power supply of the measurement apparatus, the standard solution shows an oxidation current waveform which is definitely different from a waveform which is obtained when the first potential is applied to the electrodes of the biosensor to which the sample solution is supplied, and when a second potential smaller than the first potential is applied to the electrode portion of the biosensor to which the standard solution is supplied, the standard solution shows an oxidation current waveform which is similar to a waveform which is obtained when the second potential is applied to the electrode portion of the biosensor to which the sample solution is supplied.

Therefore, it is possible to provide standard solution enabling the measurement apparatus to accomplish the identification of the kind of analyte liquid with exerting no influences on the oxidation current value flowing when the second potential is applied, which oxidation current value is a value used for controlling the precision of measurement of the measurement apparatus.

Further, the standard solution according to the present invention is one such that a value of the oxidation current which flows when the first potential is applied to the electrode portion of the biosensor to which the standard solution is supplied by the driving power supply of the measurement apparatus is larger than a value of the oxidation current which flows when the second potential is applied.

Therefore, the identification of the kind of analyte liquid can be easily accomplished on the basis of the current waveform of the oxidation current of the standard solution.

Further, according to the standard solution of the present invention, the reducing substance is oxidized when the potential of the measuring electrode is 0.1V to 1.0V higher than that of a reference electrode of Ag/AgCl.

Therefore, it is possible to provide standard solution for enabling the measurement apparatus to easily accomplish the identification of the kind of analyte liquid with no identification error occurring even when the electrode portion of the biosensor includes, in addition to the measuring electrode and the counter electrode, a reference electrode of Ag/AgCl.

Further, according to the standard solution of the present invention, the reducing substance is at least one of uric acid, bilirubin, ascorbic acid, methylene blue, Bis(2-hydroxyethyl)iminotris(hydroxymethyl)methane, N,N-Bis(2-hydroxyethyl)-2-aminoethanesulfonic acid, acetaminophen.

Therefore, it is possible to provide standard solution for enabling the measurement apparatus to easily accomplish the identification of the kind of analyte liquid with no identification error occurring, which was conventionally difficult.

Further, a determination method according to the present invention is a method for determining a substrate contained in a sample solution on the basis of an oxidation current value which is obtained by applying a first potential by a driving power supply of a measurement apparatus to an electrode portion of a biosensor including the electrode portion having a counter electrode and a measuring electrode, as well as a reagent layer reacting with the sample solution supplied to the electrode portion for a first time period, and then stopping the application for a given time period, and applying a second potential smaller than the first potential to the electrode portion for a second time period after the given time period has passed, wherein a standard solution containing a reducing substance is supplied to the electrode portion of the biosensor as a standard solution used for controlling a precision of measurement of the measurement apparatus, and it is discriminated whether a kind of analyte liquid supplied to the biosensor is the sample solution or the standard solution on the basis of the oxidation current value obtained by applying the first potential and the oxidation current value obtained by applying the second potential.

Therefore, the identification of the kind of analyte liquid by the measurement apparatus can be easily accomplished with no identification error occurring, which was conventionally difficult.

Further, according to the determination method of the present invention, when the first potential is applied to the electrode portion of the biosensor to which the standard solution is supplied, by the driving power supply of the measurement apparatus, the standard solution shows an oxidation current waveform which is definitely different from a waveform which is obtained when the first potential is applied to the electrode of the biosensor to which the sample solution is supplied, and when the second potential smaller than the first potential is applied to the electrode portion of the biosensor to which the standard solution is supplied, the standard solution shows an oxidation current waveform which is similar to a waveform which is obtained when the second potential is applied to the electrode portion of the biosensor to which the sample solution is supplied.

Therefore, the identification of the kind of analyte liquid can be easily accomplished without exerting influences on the oxidation current value flowing when the second potential is applied, which oxidation current value is a value used for controlling the precision of measurement of the measurement apparatus.

Further, according to the determination method of the present invention, the standard solution is characterized by that the value of the oxidation current which flows when the first potential is applied to the electrode portion of the biosensor to which the standard solution is supplied by the driving power supply of the measurement apparatus is larger than the value of the oxidation current which flows when the second potential is applied.

Therefore, the kind of analyte liquid can be easily identified with no identification error occurring, on the basis of the current waveform of the oxidation current of the standard solution.

Further, according to the determination method of the present invention, it is discriminated whether a kind of analyte liquid supplied to the biosensor is the sample solution or the standard solution with using ratios between oxidation current values obtained by applying the first potential and oxidation current values obtained by applying the second potential.

Therefore, the measurement apparatus can easily accomplish identification of the kind of analyte liquid with no identification error occurring, which was conventionally difficult.

Further, according to the determination method of the present invention, a discrimination parameter used for the discrimination is calculated on the basis of the oxidation current value obtained by applying the first potential and the oxidation current value obtained by applying the second potential, a discrimination function employing the discrimination parameter as an independent variable is defined, and a numeric value obtained by substituting the value of the discrimination parameter into the discrimination function is taken as a discrimination index, thereby discriminating whether a kind of analyte liquid supplied to the biosensor is the sample solution or the standard solution, on the basis of the discrimination index.

Therefore, the measurement apparatus can accomplish identification of the kind of analyte liquid with high precision and with no identification error occurring.

Further, according to the determination method of the present invention, the reducing substance is oxidized when the potential of the measuring electrode is 0.1V to 1.0V higher than that of a reference electrode of Ag/AgCl.

Therefore, the measurement apparatus can identify the kind of analyte liquid with high precision and with no identification error occurring even when the electrode portion of the biosensor includes, in addition to the measuring electrode and the counter electrode, the reference electrode of Ag/AgCl.

Further, according to the determination method of the present invention, the reducing substance is at least one of uric acid, bilirubin, ascorbic acid, methylene blue, Bis(2-hydroxyethyl)iminotris(hydroxymethyl)methane, N,N-Bis (2-hydroxyethyl)-2-aminoethanesulfonic acid, acetaminophen.

Therefore, the measurement apparatus can accomplish identification of the kind of analyte liquid with high precision and with no identification error occurring, which was conventionally difficult.

BEST MODE TO EXECUTE THE INVENTION

Embodiment 1

According to a first embodiment, the automatic identification of a kind of analyte liquid which is a target to be measured is enabled in a biosensor system in which a composition of a standard solution is improved and which has a construction similar to that of a prior art.

Hereinafter, the standard solution according to the first embodiment will be described with reference to the drawings.

Figure 1A:
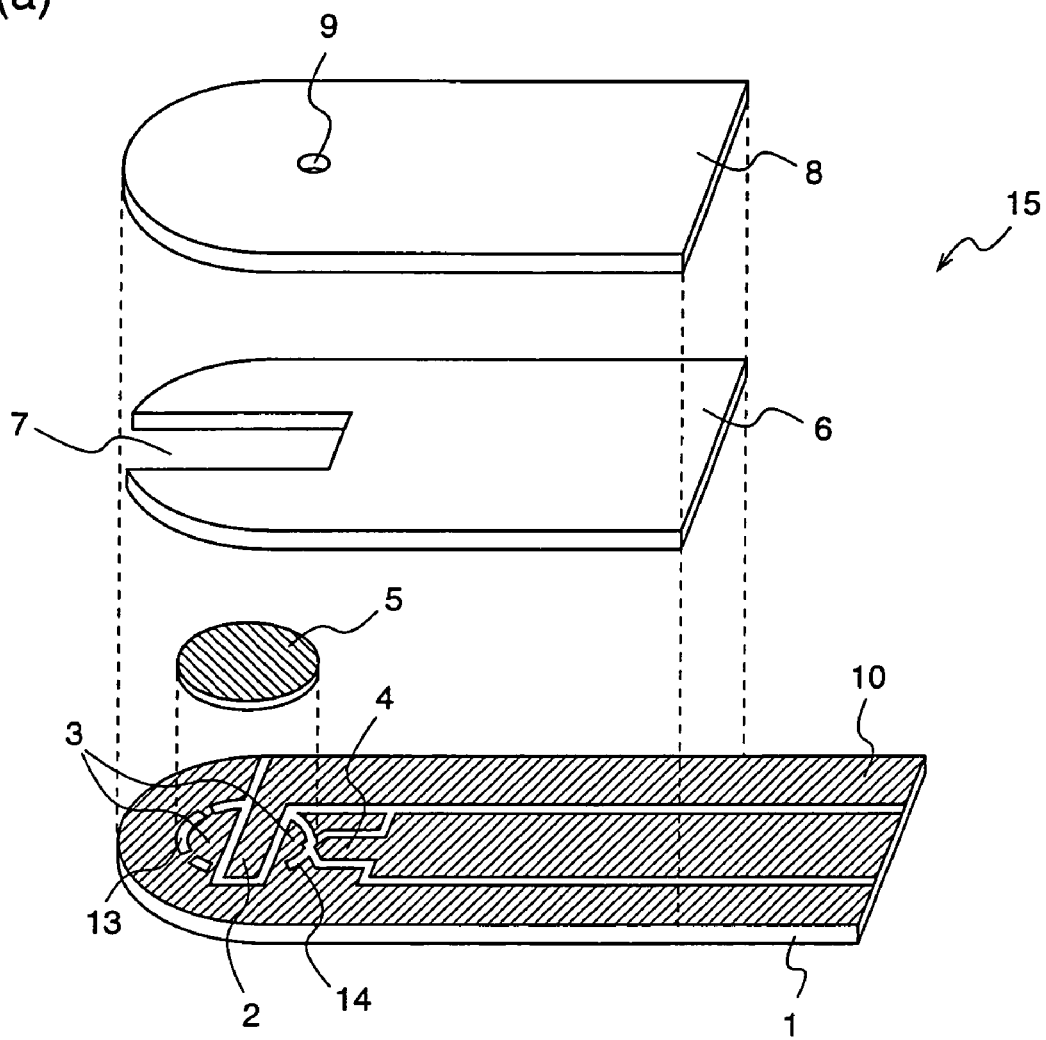
FIG. 1(a) is an exploded perspective view of a biosensor according to a prior art and a first embodiment.
Figure 1B:
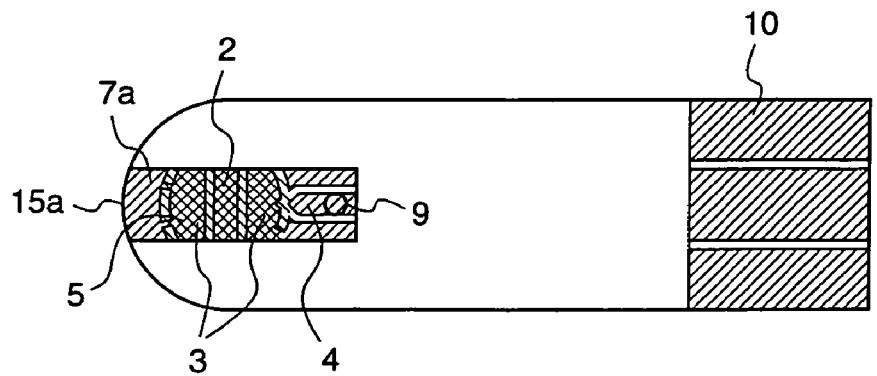
FIG. 1(b) is a plan view of the biosensor.
Figure 2:
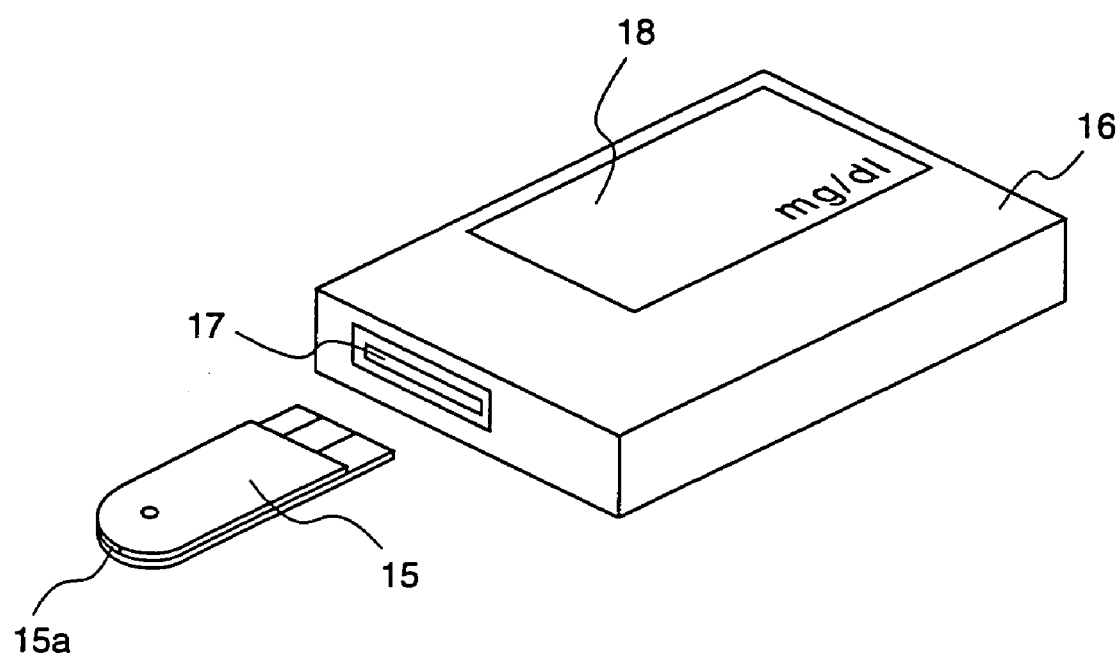
FIG. 2 is a perspective view illustrating a biosensor system according to the prior art and the first embodiment.
Figure 3A:
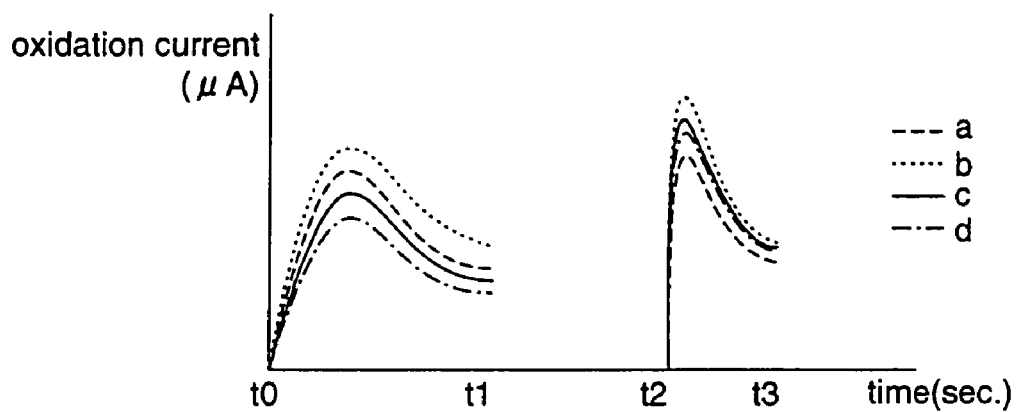
FIG. 3(a) is a diagram illustrating current waveforms of a conventional standard solution and bloods each of which has a different hematocrit value from each other.
Figure 3B:
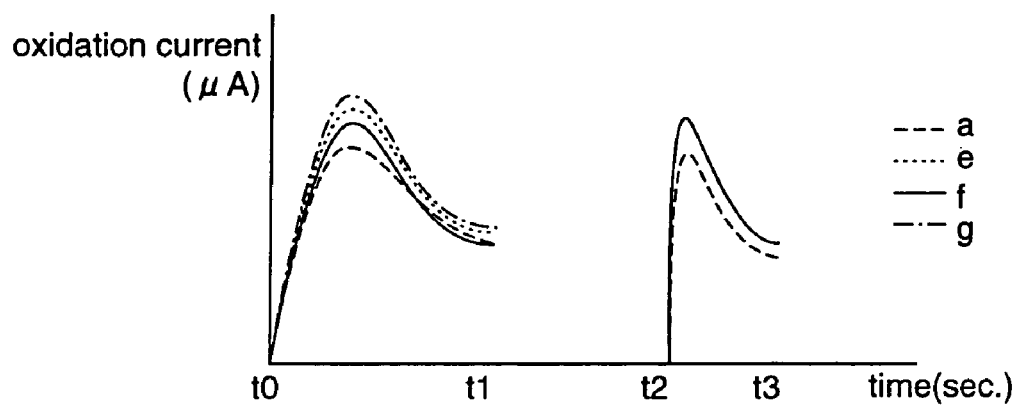
FIG. 3(b) is a diagram illustrating current waveforms of the conventional standard solution and bloods each of which contains a different interfering substance from each other.
Figure 3C:
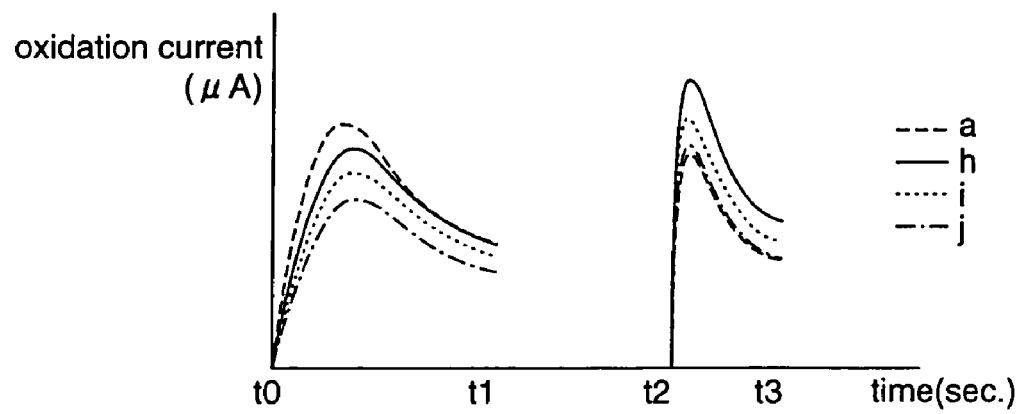
FIG. 3(c) is a diagram illustrating current waveforms of the conventional standard solution and bloods each of which has a different measurement environment from each other.
Figure 4:
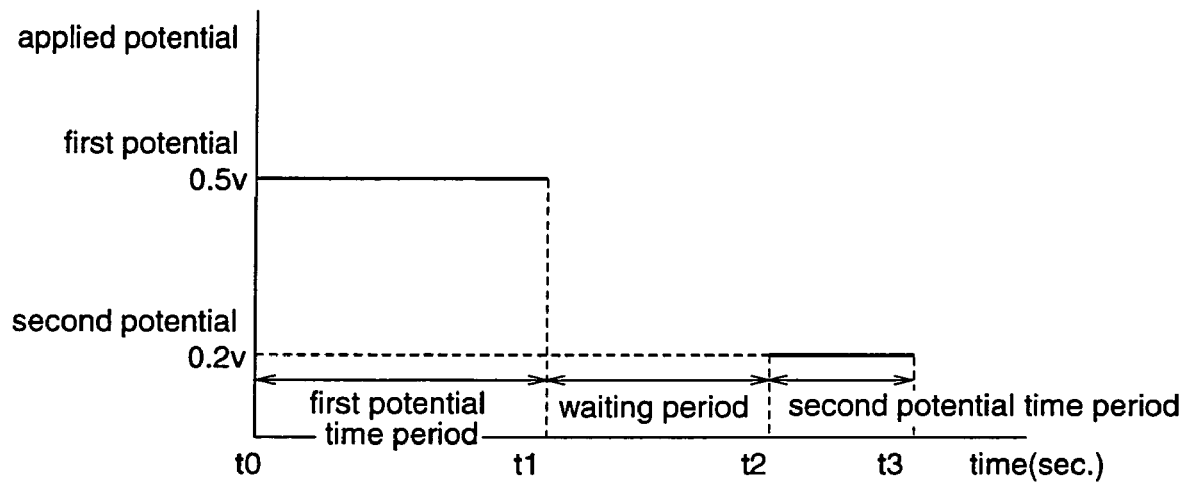
FIG. 4 is a diagram illustrating a measurement profile according to the prior art and the first embodiment.

Generally, when a precision of measurement is controlled using a standard solution in the biosensor system, the standard solution is initially spotted onto the biosensor as an analyte, and an oxidation current value is measured on the basis of the measurement profile shown in FIG. 4, and a concentration of a substrate in the standard solution is measured on the basis of only a current value at the time t3. Then, it is checked whether the measured concentration of the substrate is within a predetermined range or not, thereby controlling the precision of the measurement apparatus. Therefore, it is necessary to remain unchanged the current value of the oxidation current value of the standard solution at the time t3 and discriminate between current waveforms of a sample solution and the standard solution in order to exert no influence onto the operation for controlling the precision of the measurement apparatus as described above and automatically discriminate with high precision whether the analyte being measured is the sample solution or the standard solution.

Then, in this first embodiment, a conventional composition of the standard solution is improved so that a current value which is larger than that of the conventional standard solution is measured during the first potential time period during which the first potential shown by the measurement profile in FIG. 4 is applied and the same current value as that of the conventional standard solution is measured during the second potential time period during which the second potential is applied, thereby enabling a kind of analyte liquid being measured to be automatically identified on the basis of the oxidation current waveform of the standard solution.

Hereinafter, a composition of a standard solution and a determination method for automatically identifying a kind of analyte liquid using the standard solution according to the first embodiment will be described.

Initially, a description will be given with the composition of the standard solution according to the first embodiment and the composition of the conventional standard solution being compared.

(Conventional Composition of Standard Solution)

Initially, three types of glucoses, that is, a glucose having a lower concentration of 40 mg/dL, a glucose having an intermediate concentration of 120 mg/dL, and a glucose having a higher concentration of 350 mg/dL, are provided as glucoses of the predetermined amounts, which are used for measuring glucose. Then, each of the predetermined amounts of glucoses, 0.1 wt % of xanthan gum of water-soluble high polymer as thickener, 0.05 wt % of SUPELCO's ProClin as preservative, 0.04 wt % of Red No. 4 as colorant are compounded with buffer solution controlled as pH7.0, which buffer solution is prepared from disodium hydrogenphosphate of 65 mM and sodium dihydrogenphosphate of 35 mM, as buffer, thereby preparing 3 types of standard solutions each of which has a different concentration of glucose from each other.

(Composition of Standard Solution According to the Present Invention)

The standard solution of the present invention is obtained by eliminating disodium hydrogenphosphate and sodium dihydrogenphosphate as buffer from the conventional standard solution, and adding 50 mM of Bis (2-hydroxyethyl) iminotris (hydroxymethyl)methane (hereinafter, merely referred to as Bis-Tris) as reducing substance instead thereof, and further adding hydrochloric acid, and controlling the resultant as pH7.0. Except for this, each of three types of glucoses of the predetermined amounts, thickener, preservative, and colorant are compounded, thereby preparing three types of standard solutions each of which has a different concentration of glucose from each other, just as with the conventional standard solution. Then, for the standard solution of the present invention, hydrochloric acid is added to the Bis-Tris which is compounded as reducing substance, the resultant is controlled as pH7.0 and the controlled resultant acts as buffer, and therefore it is not necessary to add phosphoric acid buffer.

Figure 5:
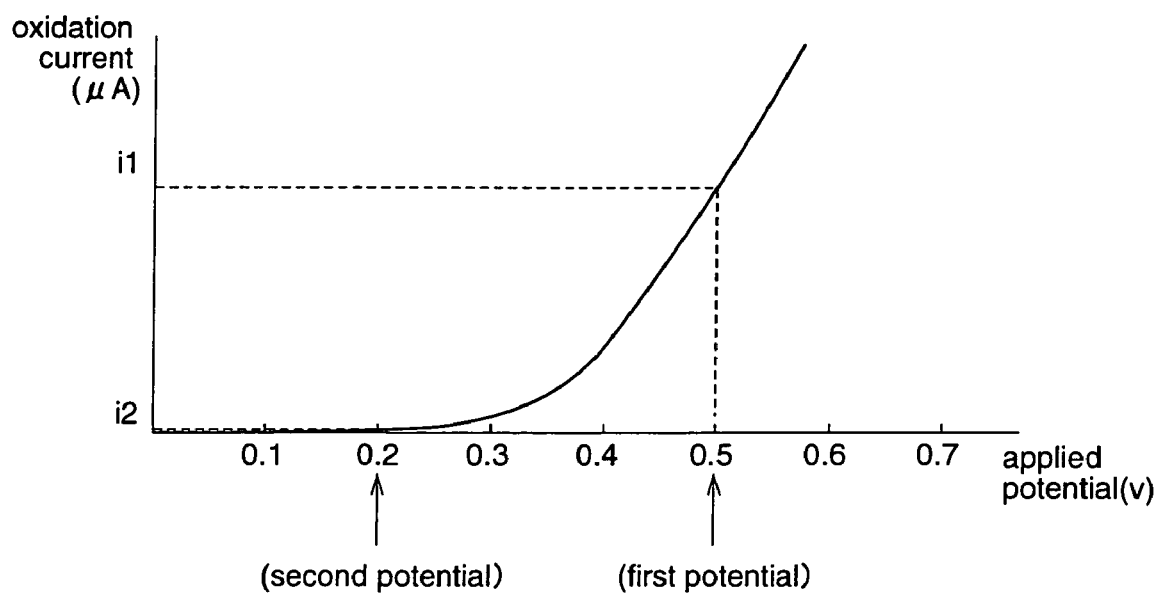
FIG. 5 is a diagram illustrating an oxidation current-potential curve of a reducing substance according to the first embodiment of the present invention.

An oxidation current that is generated when spotting water-solution of the reducing substance which is added to the standard solution according to the first embodiment onto the biosensor and sweeping a voltage applied between the counter electrode 3 and the measuring electrode 2 of the biosensor from 0.1V to 0.7V becomes as shown in FIG. 5.

As is apparent from FIG. 5, the current value of the standard solution having added the reducing substance according to the first embodiment becomes larger with the applied voltage becoming higher.

Figure 6:
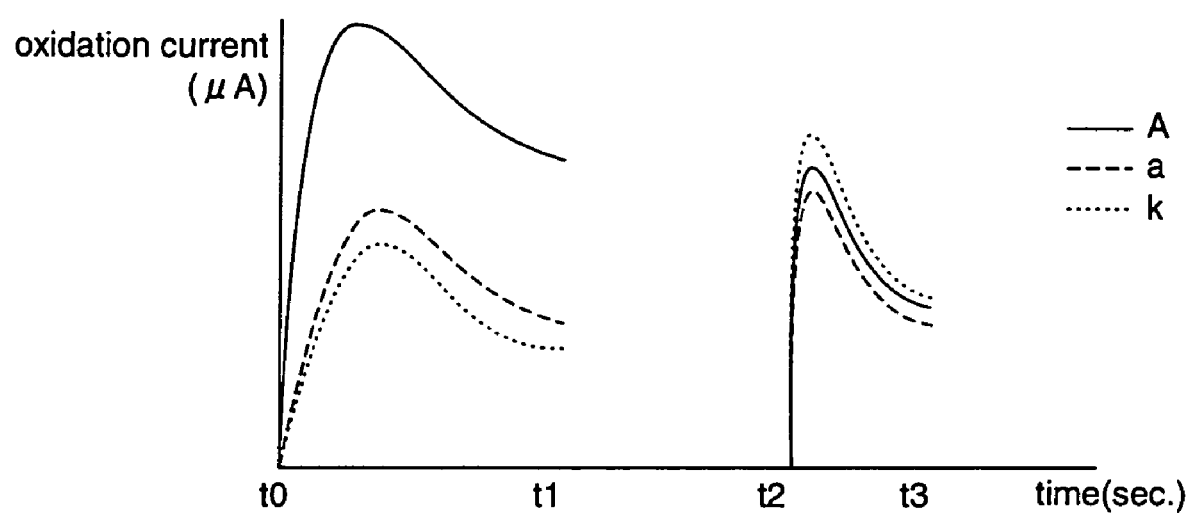
FIG. 6 is a diagram illustrating current waveforms of a standard solution according to the first embodiment of the present invention, the conventional standard solution, and a typical blood.

Therefore, when the standard solution of the first embodiment having such reducing substance added is measured according to the measurement profile shown in FIG. 4, the oxidation current generated from the reducing substance flows a lot during a period when the first potential is applied (a first potential time period), and then a current value i1 detected when the first potential shown in FIG. 5 is applied is added to the oxidation current generated by a reaction between an enzyme and a glucose contained in the standard solution to detect a larger oxidation current, as shown by the current waveform of the standard solution according to the first embodiment. FIG. 6 is a diagram illustrating waveforms of the oxidation current values measured when voltages are applied to the biosensors onto which a standard solution A according to the first embodiment, a conventional standard solution a, and a typical blood (a blood having a hematocrit value of 45%)k are spotted, respectively, in the biosensor system. As shown in FIG. 6, the standard solution A according to the first embodiment has almost the same current waveform as the conventional standard solution a for the second potential time period, while it exhibits a current value higher than those of the conventional standard solution a and the blood analyte k being detected as a current value for the first potential time period. Therefore, the use of the standard solution according to the first embodiment enables the measurement apparatus 16 to securely and automatically discriminate between the standard solution and the blood analyte, which is conventionally difficult.

Then, as the method for identifying a kind of analyte liquid, it is only required to simply compare ratios between current values for the second potential time period and current values for the first potential time period of the respective obtained current waveforms with each other, and a solution having the largest ratio may be judged as the standard solution.

However, as the described above, the respective analytes to be measured by the biosensor system have various different conditions such as having different hematocrit values and different contents of interfering substances, and thereby there may be some cases where it is not possible to obtain the ratio which can serve as an index for identifying a kind of analyte liquid with high precision by merely comparing the ratios between the current values for the first potential time period and the current values for the second potential time period of plural current waveforms detected when the standard solution according to the first embodiment is used. Then, in the first embodiment, each analyte is identified by a discrimination method using a discrimination function, not by merely comparing the ratios between the current values for the first potential time period and the current values for the second potential time period of the respective analytes.

That is, a discrimination parameter used for the discrimination is calculated on the basis of the current values which are measured under three consecutive application conditions of the first potential time period of 6 seconds, the waiting period of 6 seconds, and the second potential time period of 3 seconds as shown by the measurement profile in FIG. 4 and a discrimination function employing the calculated discrimination parameter as an independent variable is defined, and a numeric value which is obtained by substituting the value of the discrimination parameter into the discrimination function is taken as a discrimination index, and a kind of analyte liquid is identified on the basis of the discrimination index.

Then, a specific discrimination function is created in a similar manner to the embodiment of the above-described International Application Publication No. WO01/40787A1, and a discrimination parameter is calculated on the basis of a current waveform obtained when the blood anayte is measured, and a discrimination parameter is similarly calculated on the basis of a current waveform obtained when standard analyte liquid is measured, thereby to set a linear function which takes the largest difference between the two groups as the discrimination function.

While the discrimination parameter and discrimination function used here vary for each composition of the standard solution, specifically a ratio between a current for the first potential time period and a current for the second potential time period is used as at least one of the discrimination parameters, thereby facilitating the discrimination between the standard solution and the blood analyte.

Tables 1 and 2 illustrate that a kind of analyte liquid is actually identified with using the standard solution of the present invention and the conventional standard solution, respectively.

The measured analytes are three standard solutions of concentrations of 40 mg/dL, 120 mg/dL, and 350 mg/dL, and 18 analytes obtained by controlling 6 kinds of blood analytes of glucose concentrations of 40 mg/dL, 80 mg/dL, 120 mg/dL, 200 mg/dL, 350 mg/dL, 420 mg/dL so that each of the blood analytes has three Hct concentrations (20%, 45%, 60%).

For each analyte, 20 sensor lots each of which has a different production date from each other are used to repeat the evaluation 10 times for each sensor lot. Then, for the standard solution, 20 sensor lots each of which has a different production date from each other are used to execute the evaluation 20 times for each sensor lot.

The result of the evaluations in the case of using the standard solution of the present invention and the result of the evaluations in the case of using the conventional standard solution are as shown in (Table 1) and (Table 2), respectively.

TABLE 1

The result of the discrimination in the case of using the standard solution of the present invention

| | Discrimination Result | |
|---|---|---|
| Sample | Standard solution | Blood |
| Standard solution of the present invention | 1200 | 0 |
| Blood | 0 | 3600 |

TABLE 2

The result of the discrimination in the case of using the conventional standard solution

| | Discrimination Result | |
|---|---|---|
| Sample | Standard solution | Blood |
| Conventional standard solution | 1195 | 5 |
| Blood | 1 | 3599 |

Consequently, while some error in discrimination occurs when the discrimination is performed using the conventional standard solution, the discrimination with very high precision becomes possible with using the standard solution containing the reducing substance of the present invention.

As described above, according to the first embodiment, the standard solution containing reducing substance is used as a standard solution, and thereby the oxidation current of the standard solution is larger than that of the conventional standard solution for the first potential time period. Accordingly, the ratios between the oxidation currents flowing for the second potential time period and the oxidation currents flowing for the first potential time period are merely compared with each other, thereby facilitating discrimination between the standard solution and the blood which is the sample solution, which enables the measurement apparatus 16 to automatically identify a kind of analyte liquid. Further, the use of the above-described discrimination function enables the kind of analyte liquid to be automatically identified with higher precision.

Then, while in the first embodiment the first potential is 0.5V and the second potential is 0.2V, since the oxidation current-potential curve behavior of the water-solution in which the reducing substance is dissolved as shown in FIG. 5 is differently exhibited due to various influences of electrodes of the biosensor 15 used for the measurement, a kind of reducing substance, a viscosity of the water-solution in which the reducing substance is dissolved, a pH, an environmental temperature, or the like, a combination of the first and second potentials to be applied to the biosensor 15, which generates the oxidation current i2 which is smaller than the oxidation current i1, may be selected on the basis of the oxidation current-potential curve behavior of the water-solution in which the reducing substance added to the standard solution is dissolved, which curve is measured by sweeping the applied voltage. Then, a combination which makes the oxidation current i1 larger than the oxidation current i2 by 1 μA or more is appropriate as a combination of the first and second potentials, and particularly an effect with higher precision could be achieved by a combination which makes the oxidation current i1 larger than the oxidation current i2 by 5 μA.

Further, while a case where the reducing substance contained in the standard solution of this embodiment is Bis-Tris is taken as an example, the reducing substance is not restricted thereto.

That is, as long as a reducing substance to be added to the standard solution according to the first embodiment is a substance by which an oxidation current flows when the first potential is applied between the measuring electrode 2 and the counter electrode 3 and an oxidation current smaller than an oxidation current which flows when the first potential is applied flows when the second potential smaller than the first potential is applied, in the biosensor, the same effect as the above can be achieved.

For example, even when the reducing substance is any one of uric acid, bilirubin, ascorbic acid, methylene blue, acetaminophen, and the like, the similar effect can be expected.

Further, while in this first embodiment Good's buffer solution which is obtained by adding hydrochloric acid to the reducing substance Bis-Tris as Good's buffer and controlling the resultant as pH7.0 is used as buffer solution, even when Good's buffer solution is prepared for use from any one of N,N-Bis(2-hydroxyethyl)-2-aminoethanesulfonic acid (hereinafter, merely referred to as BES), ADA, MOPS, MOPSO, TAPSO, TES, ACES or the like, which are other Good's buffer, it is confirmed that the same effect can be achieved.

Further, while in the first embodiment a case where the reducing substance, Bis-Tris of 50 mM is compounded is described, as long as an amount of Bis-Tris which can be easily dissolved is compounded, the same effect can be achieved, and it is appropriate that the compound concentration is 1 mM to 200 mM, and it is more preferable that the compound concentration be 10 mM to 100 mM. Then, since an amount of oxidation current generated from the reducing substance is in proportion to the compound concentration of the reducing substance, a reducing substance corresponding to an amount of oxidation current which is required for enabling discrimination from other blood analytes may be arbitrarily compounded.

Further, while in the first embodiment it is described that a voltage is applied between the counter electrode 3 and the measuring electrode 2 of the biosensor 15, a biosensor including Ag/AgCl as a reference electrode in the notch 7 of the biosensor (not shown) may be used so as to achieve a result with higher precision. In the case of using such a biosensor, when a reducing substance which generates an oxidation current when the potential of the measuring electrode is 0.1V to 1.0V higher than that of the reference electrode provided with the biosensor is used as a reducing substance to be compounded with the standard solution, the same effect can be achieved.

APPLICABILITY IN INDUSTRY

The determination method and the standard solution according to the present invention is very useful as ones which eliminate an error in identifying a kind of analyte liquid when a measurement apparatus for a biosensor itself automatically discriminates whether the kind of analyte liquid is a standard solution or a sample solution in a biosensor system comprising the biosensor and the measurement apparatus for the biosensor.

The invention claimed is:

1. A method for determining a substrate contained in a sample solution on the basis of an oxidation current value, the method comprising:

applying a first potential from a driving power supply of a measurement apparatus to an electrode portion of a biosensor for a first time period, the biosensor including the electrode portion, which comprises a counter electrode and a measuring electrode, and a reagent layer, which reacts with the sample solution supplied to the electrode portion;

stopping the application of the first potential for a given time period; and applying a second potential, which is smaller than the first potential, to the electrode portion for a second time period after the given time period has passed;

determining whether a kind of analyte liquid supplied to the biosensor is the sample solution or a standard solution based on the oxidation current value obtained by applying the first potential and the oxidation current value obtained by applying the second potential, wherein the standard solution is supplied to the electrode portion of the biosensor as the standard solution is used for controlling a precision of measurement of the measurement apparatus, wherein when the first potential is applied to the electrode portion of the biosensor to which the standard solution is supplied by the driving power supply of the measurement apparatus, the standard solution shows an oxidation current waveform which is definitely different from a waveform which is obtained when the first potential is applied to the electrode portion of the biosensor to which the sample solution is supplied, wherein when the second potential is applied to the electrode portion of the biosensor to which the standard solution is supplied, the standard solution shows an oxidation current waveform which is approximately the same as a waveform which is obtained when the second potential is applied to the electrode portion of the biosensor to which the sample solution is supplied, wherein the standard solution is one such that the value of the oxidation current, which flows when the first potential is applied to the electrode portion of the biosensor to which the standard solution is supplied by the driving power supply of the measurement apparatus, is larger than the value of the oxidation current which flows when the second potential is applied, and wherein the standard solution includes a reducing substance and a predetermined amount of substrate, and the precision of measurement of the measurement apparatus controlled by checking whether a measured substrate concentration is within a predetermined range or not.

2. The determination method as defined in claim 1, wherein, the determination as to whether a kind of analyte liquid supplied to the biosensor is the sample solution or the standard solution is based on ratios between oxidation current values obtained by applying the first potential and oxidation current values obtained by applying the second potential.

3. The determination method as defined in claim 1, wherein a discrimination parameter used for the determination is calculated on the basis of the oxidation current value obtained by applying the first potential and the oxidation current value obtained by applying the second potential, a discrimination function employing the discrimination parameter as an independent variable is defined, and a numeric value obtained by substituting the value of the discrimination parameter into the discrimination function is taken as a discrimination index, thereby determining whether the kind of analyte liquid supplied to the biosensor is the sample solution or the standard solution, on the basis of the discrimination index.

4. The determination method as defined in claim 1, wherein the reducing substance is oxidized when the potential of the measuring electrode is 0.1V to 1.0V higher than that of a reference electrode of Ag/AgCl.

5. A method for determining a substrate contained in a sample solution on the basis of an oxidation current value, the method comprising:

applying a first potential from a driving power supply of a measurement apparatus to an electrode portion of a biosensor for a first time period, the biosensor including the electrode portion, which comprises a counter electrode and a measuring electrode, and a reagent layer, which reacts with the sample solution supplied to the electrode portion;

stopping the application of the first potential for a given time period; and applying a second potential, which is smaller than the first potential, to the electrode portion for a second time period after the given time period has passed;

determining whether a kind of analyte liquid supplied to the biosensor is the sample solution or a standard solution based on the oxidation current value obtained by applying the first potential and the oxidation current value obtained by applying the second potential, wherein the standard solution is supplied to the electrode portion of the biosensor as the standard solution is used for controlling a precision of measurement of the measurement apparatus, wherein the standard solution includes a reducing substance and a predetermined amount of substrate, and the precision of measurement of the measurement apparatus is controlled by checking whether a measured substrate concentration is within a predetermined range or not, and wherein the reducing substance is at least one of uric acid, bilirubin, ascorbic acid, methylene blue, Bis(2-hydroxyethyl)iminotris(hydroxymethyl)methane, N, N-Bis(2-hydroxyethyl)-2-aminoethanesulfonic acid, and acetaminophen.

6. The determination method as defined in claim 5, wherein the determination as to whether a kind of analyte liquid supplied to the biosensor is the sample solution or the standard solution is based on ratios between oxidation current values obtained by applying the first potential and oxidation current values obtained by applying the second potential.

7. The determination method as defined in claim 5, wherein a discrimination parameter used for the determination is calculated on the basis of the oxidation current value obtained by applying the first potential and the oxidation current value obtained by applying the second potential, a discrimination function employing the discrimination parameter as an independent variable is defined, and a numeric value obtained by substituting the value of the discrimination parameter into the discrimination function is taken as a discrimination index, thereby determining whether the kind of analyte liquid supplied to the biosensor is the sample solution or the standard solution, on the basis of the discrimination index.

8. The determination method as defined in claim 5, wherein the reducing substance is oxidized when the potential of the measuring electrode is 0.1V to 1.0V higher than that of a reference electrode of Ag/AgCl.

* * * * *